United States Patent [19]
Johnson, Jr.

[11] 4,286,457
[45] Sep. 1, 1981

[54] VISCOSITY MEASUREMENT
[75] Inventor: Henry W. Johnson, Jr., Sugar Land, Tex.
[73] Assignee: Shell Oil Company, Houston, Tex.
[21] Appl. No.: 127,701
[22] Filed: Mar. 6, 1980
[51] Int. Cl.³ .................. G01N 31/08; G01N 33/44
[52] U.S. Cl. ...................................... 73/53; 73/54; 73/61.1 C
[58] Field of Search ............... 73/53, 54, 55, 61.1 C
[56] References Cited
U.S. PATENT DOCUMENTS

| 3,420,096 | 1/1969 | Hoyt | 73/54 |
| 3,649,200 | 3/1972 | Moore | 73/61.1 C X |
| 3,683,678 | 8/1972 | Yau | 73/53 |
| 3,837,217 | 9/1974 | Schulz | 73/53 X |
| 3,924,448 | 12/1975 | Howard et al. | 73/53 X |
| 4,258,564 | 3/1981 | Hulme et al. | 73/61.1 C |

*Primary Examiner*—Gerald Goldberg
*Assistant Examiner*—Joseph W. Roskos

[57] ABSTRACT

A method and apparatus for determining the solution viscosity of polymers using gel partition chromatography (GPC). The method comprises obtaining a GPC analysis of the solution and measuring the pressure drop at a selected point in the GPC flow path. The GPC analysis provides a measure of the polymer concentration in the solution. The viscosity can be determined from the pressure drop in combination with the known polymer concentration.

4 Claims, 2 Drawing Figures

VISCOSITY MEASUREMENT

BACKGROUND OF THE INVENTION

The present invention pertains to a method and apparatus for determining the solution viscosity of polymers. The solution viscosity of polymers is very important in the manufacturing of various polymers. It is used to determine if the molecular weight of the polymer is correct and that the distribution of various molecular weight components within the polymer are correct. The molecular weight of the polymer is important in the control of the production of the polymer.

In the past, various methods have been suggested for determining the solution viscosity of polymers. One approach has been the drying of a polymer sample, dissolving a known amount of the sample in a selected solvent and determining the viscosity of the solution. This requires precise temperature equilibrium of the solution and the elimination of any gas bubbles or incompletely / dissolved polymer in the solvent. Also, attempts have been made to estimate the viscosity from the pressure drop produced by the introduction of a sample of the polymer into a solvent stream. These attempts are only approximate unless it is possible to simultaneously measure the polymer concentration to ensure that the polymer concentration in the solution remains constant. In the absence of measurements of the polymer concentration in the solvent it is impossible to determine the solution viscosity.

BRIEF SUMMARY OF THE INVENTION

The present invention solves the above problems by providing a method for determining the polymer concentration in the solvent and at the same time measuring the pressure drop due to the presence of the polymer. In particular, the invention utilizes a liquid gel partitioned chromatograph to measure the polymer concentration in the solvent. At the same time the pressure drop caused by the presence of the polymer in the solvent is measured in the waste disposal line of the chromatograph. Normally, it is desirable to have a chromatograph record of the polymer and using the present invention the solution viscosity can be obtained at the same time without additional effort or time.

The chromatograph of the invention is designed to permit the dissolving of a polymer sample in a suitable solvent while controlling the flow rate and mixing of the dissolved polymer so that an accurate chromatographic record of the polymer may be obtained. A particularly suitable chromatograph is one manufactured by Applied Automation Company of Bartlesville, Okla. This chromatograph is provided with means for on-line dilution and filtration of polymer samples prior to the chromatographic analysis. In particular, the instrument is provided with accurate flow controllers to obtain constant flow rates and suitable mixing chambers to mix the polymer sample with the solvent. The chromatograph has been modified to provide a pressure transducer in the discharge line of the diluted polymer on the upstream side of the flow control capillary in the discharge line. The signal from the pressure transducer and from the chromatograph analysis are recorded on the same chart record and to the same time base so that an accurate correlation can be made between the polymer solids present in the sample and the pressure drop resulting from the presence of the polymer. From the correlation, one can then determine the solution viscosity of the polymer.

BRIEF DESCRIPTION OF THE DRAWINGS

The present invention will be more easily understood from the following detailed description when taken in conjunction with the attached drawings in which.

DESCRIPTION OF A PREFERRED EMBODIMENT

Figure 1:
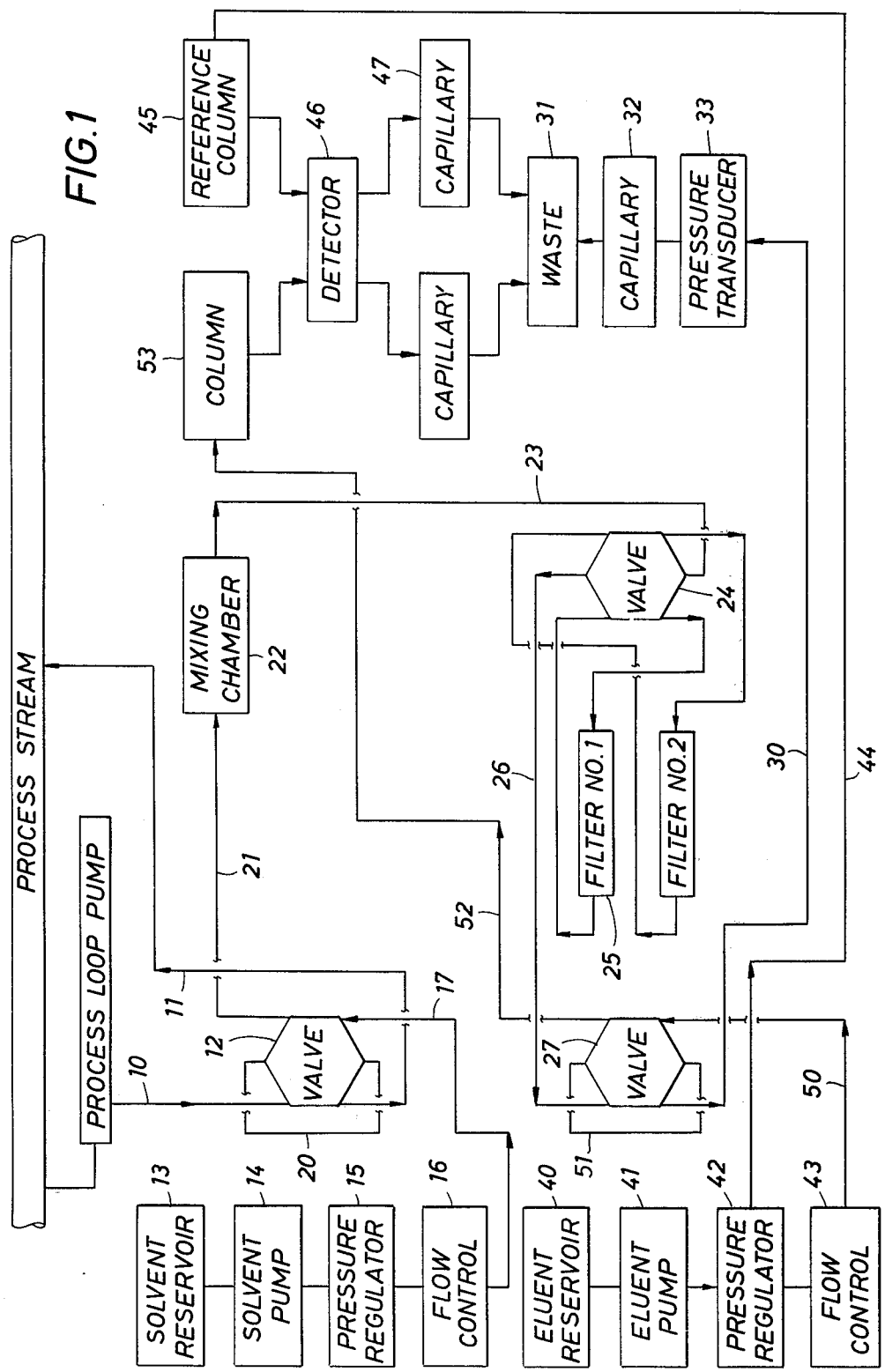
FIG. 1 is a schematic drawing of the modified chromatograph of the present invention; and, FIG. 2 is a sample chart record of the instrument of FIG. 1.

Referring now to FIG. 1, there is shown a conventional liquid gel partition chromatograph of the type manufactured by Applied Automation, Inc. The chromatograph is designed to take a sample from a process stream through a sample line 10 and return it to the process stream through line 11. A process loop pump is used to remove the sample from the stream and provide sufficient pressure to return it to the process stream. A supply of solvent is provided in a reservoir 13 and supplied to the chromatograph by pump 14. The solvent pressure is controlled by a pressure regulator 15 and a flow control 16. Both the flow controller and pressure regulator are located in a constant temperature compartment so that an accurate flow of solvent at a constant is maintained. It is a necessary requirement of this invention that each component following the regulators 15 and 42 be at a constant temperature, although different temperatures can be maintained for different components if desired. The solvent flows through line 17 which is connected to the two position valve 12. The solvent flows from the valve 12 through line 21 to a mixing chamber 22 and then by line 23 to a second two position valve 24. From the valve 24 the solvent flows through a filter 25 and then back to the valve 24 through a line 26 to a third two position valve 27. All of the valves 12, 24 and 27 are conventional chromatography valves which have multiple positions so that flow streams can be directed to various portions of the equipment or samples contained in sample loops can be injected into the equipment by directing a flow of suitable fluid through the valve. From valve 27, the solvent flows through a line 30 to a waste disposal 31. Mounted in the line 30 before the waste disposal is a capillary 32 and a pressure transducer 33. The capillary serves to further control the flow rate of the solvent while the pressure transducer measures the pressure in the solvent line and particularly the pressure drop caused by the passage of a polymer sample.

The polymer sample is injected into the chromatograph system from the sample loop 20 through which the process stream normally flows. By properly positioning the valve 12, the sample contained in the sample loop 20 can be isolated and then transported by the solvent in the line 17 to the mixing chamber 22. The process stream sample is mixed with a solvent in the chamber 22 and then transported through the valve 24 and filter 25 to the valve 27. Valve 27 is also provided with a sample loop 51 through which the diluted process stream sample normally flows. Thus, the diluted sample of the polymer from the process stream will flow through the line 30 and be disposed in the waste disposal 31. In passing to the waste disposal 31 the pressure increase caused by the polymer sample will be measured by the pressure transducer 33.

The chromatograph is also supplied with an eluent in reservoir 40 having a pump 41, pressure regulator 42 and flow control 43. The eluent serves to transport a sample of the diluted polymer from the process stream to the chromatograph column and detector. In particular, the eluent from the flow control 43 is passed by a line 50 to the valve 27 where it can serve to transport the sample contained in the sample loop 51 via the line 52 to the column 53. Again, the valve 27 should be positioned so that the eluent can transport the measured sample to the column 53. Column 53 is packed with a suitable gel, for example, Waters Associates MicroBondagel column E-500. The column will separate the polymer according to the size of the molecules contained in the polymer sample and elute them from the bottom of the column to the detector 46. Detector 46 can be any type of detector but preferably an ultraviolet or refractive index detector. As shown in the drawings, the eluent is taken from the pressure regulator 42, passed through a line 44 to a reference column 45 which is also connected to the detector 46. Both of the discharges from the detector are passed through capillaries 47 to the waste disposal 31. Capillaries 47 again serve to further control the flow of both the sample containing portion of the steam and the reference stream.

Figure 2:
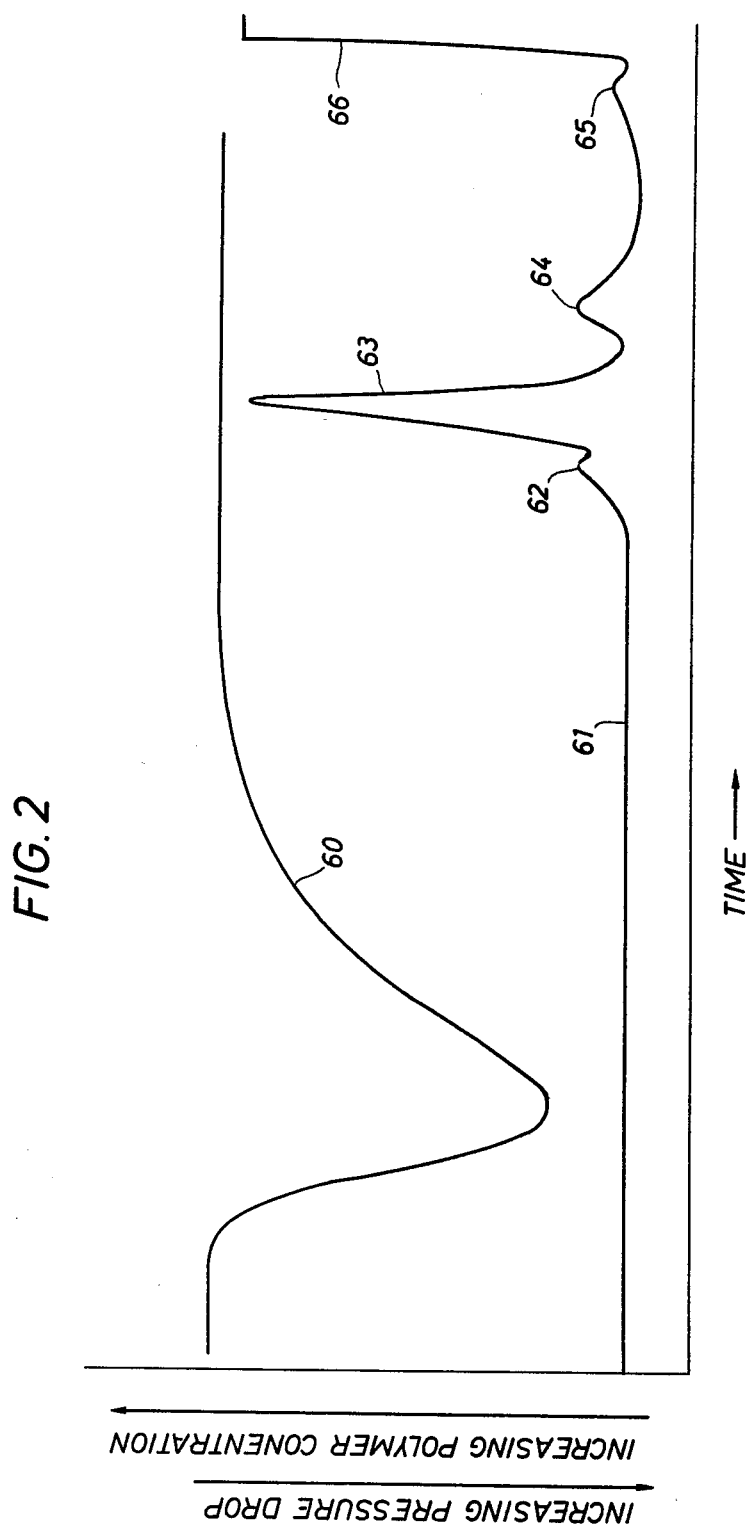

While not shown in FIG. 1, the signal from the pressure transducer 33 and the detector 46 are supplied to a chart recorder having a pair of pens so that both the pressure of the solvent stream containing the process sample as well as the output from the chromatograph can be recorded in a correlatable manner. A representative recording is shown in FIG. 2 in which the curve 60 illustrates the pressure as measured by the pressure transducer while the curve 61 illustrates the signal from the detector 46. The chromatograph signal is shown as having four peaks 62–65 that represent the various molecular weights of the polymer contained in the sample. Also shown is a dilution solvent peak 66 at the right of the plot which goes off scale. By integrating the area under the peaks, one can obtain a representation of the total polymer contained in the sample. This representation can then be correlated with the pressure reduction caused by the passage of the polymer sample through the pressure transducer to obtain the solution viscosity of the polymer. This peak of pressure increase is represented by the upside-down peak in the pressure transducer recording 60.

From the above description of the chromatograph apparatus used in the present invention, it is appreciated that the polymer sample concentration will reach a maximum and then slowly decay on an exponential curve as additional solvent is added to the mixing chamber. This relationship is clearly shown in the pressure curve 60 of FIG. 2 where there is a sudden increase in the pressure of the solvent stream as the initial portion of the polymer sample passes through the pressure transducer and then an exponential increase in pressure. It is apparent that the actual height of the peaks and the area under the peaks in the chromatograph curve of FIG. 2 depend upon the time that elapses between the opening of the valve 12 to inject the sample into the mixing chamber 22 and the opening of the valve 27 to inject the sample into the chromatograph column 53. This variable can be controlled accurately maintaining the same time interval between the opening of the two valves.

In addition to the above, several modifications can be made to the equipment. For example, one could provide a continuous detector in the solution stream after the capillary 32 to provide a continuous measurement of the concentration of the polymer in the diluent stream. This provides an indication of variation in concentration of polymer with time. Of course, it would also be possible using this approach to eliminate the chromatograph column though normally, a composition analysis of a polymer is also desired. Also, instead of using the areas of the peaks to determine the concentration of polymer in the sample, one could use the peak heights although this would probably not be as accurate.

What is claimed is:

1. A method for determining the solution viscosity of a polymer comprising:
   performing a gel partition chromatography analysis of the polymer solution;
   measuring the pressure drop in the flow line to the chromatography column caused by the passage of said polymer solution; and,
   recording both said analysis and pressure drop in a correlatable manner.

2. The method of claim 1 and in addition diluting and filtering the polymer before measuring the pressure drop.

3. The method of claim 1 wherein both said pressure drop measurement and said analysis are recorded on the same time scale.

4. An apparatus for determining the solution viscosity of a polymer comprising:
   a chromatography apparatus including means for supplying a solvent stream for diluting a sample of the polymer,
   means disposed in said solvent stream to control the flow of said solvent at a constant temperature;
   sample means for supplying a sample of the diluted polymer to the chromatography column;
   a discharge line for discharging the portion of said solvent and diluted polymer not used as a sample;
   a capillary disposed in said discharge line to regulate the flow therein; and,
   a pressure transducer disposed in said discharge line upstream of said capillary to measure the pressure therein.

* * * * *